US006294699B1

(12) United States Patent
Refvik et al.

(10) Patent No.: US 6,294,699 B1
(45) Date of Patent: Sep. 25, 2001

(54) OXIDATION OF MERCAPTANS TO ORGANIC DISULFIDES

(75) Inventors: Mitchell D. Refvik; James Edward Shaw, both of Bartlesville, OK (US)

(73) Assignee: Richmond, Hitchcock, Fish & Dollar, Bartlesville, OK (US)

( * ) Notice: Subject to any disclaimer, the term of this patent is extended or adjusted under 35 U.S.C. 154(b) by 0 days.

(21) Appl. No.: 09/539,583

(22) Filed: Mar. 31, 2000

Related U.S. Application Data

(63) Continuation-in-part of application No. 09/385,570, filed on Aug. 30, 1999.

(51) Int. Cl.⁷ .................................................. C07C 321/00
(52) U.S. Cl. .............................. 568/26; 568/21; 568/23; 568/25
(58) Field of Search ................................ 568/21, 23, 25, 568/26

(56) References Cited

U.S. PATENT DOCUMENTS 5,026,915 * 6/1991 Buchholz et al. ..................... 568/26

* cited by examiner

Primary Examiner—Johann Richter
Assistant Examiner—J. Parsa
(74) Attorney, Agent, or Firm—Jeffrey R. Anderson; Charles W. Stewart

(57) ABSTRACT

A process useful for producing an organic disulfide is disclosed. The process can include contacting mercaptans with a solid catalyst selected from the group consisting of a Group IIA metal oxide; 2) an alumina material consisting essentially of alumina; 3) an impregnated alumina impregnated with a metal selected from the group consisting of cobalt, molybdenum, tungsten, nickel and combinations of any two or more thereof; 4) an acidic ion-exchange resin; 5) a basic ion-exchange resin; and 6) combinations of any two or more thereof; in the presence of sulfur dioxide and in the substantial absence of a liquid oxidation catalyst to thereby produce organic disulfides. Alternatively, the process can include contacting mercaptans with a solid catalyst selected from the group consisting of 1) a Group IIA metal oxide; 2) alumina; 3) an impregnated alumina impregnated with a metal selected from the group consisting of cobalt, molybdenum, tungsten, nickel and combinations of any two or more thereof; 4) an acidic ion-exchange resin; 5) a basic ion-exchange resin; and 6) combinations of any two or more thereof; in the presence of sulfur dioxide, in the presence of an oxygenated hydrocarbon, and, optionally, in the substantial absence of a liquid oxidation catalyst, to thereby produce organic disulfides.

80 Claims, No Drawings

OXIDATION OF MERCAPTANS TO ORGANIC DISULFIDES

This application is a continuation-in-part of application Ser. No. 09/385,570, filed Aug. 30, 1999.

FIELD OF THE INVENTION

The invention relates to a process for producing organic disulfides by oxidation of mercaptans.

BACKGROUND OF THE INVENTION

Organic disulfides are useful as chemicals for pre-sulfiding catalysts and as chemical intermediates in the production of agricultural and pharmaceutical products. Organic disulfides are produced by oxidation of mercaptans according to the general reaction:

$$2\text{R-SH} + \text{Oxidant} \rightarrow \text{R-S-S-R} + \text{Reductant}, \quad (1)$$

wherein R is a hydrocarby radical.

The most common oxidants for consideration are sulfur, hydrogen peroxide, a reducible metal ion, oxygen and sulfur dioxide.

Examples of these are as follows:

| | |
|---|---|
| 2 R-SH + S → R-S-S-R + H$_2$S | (2) |
| 2 R-SH + H$_2$O$_2$ → R-S-S-R + 2 H$_2$O | (3) |
| 2 R-SH + 2 Fe$^{+3}$ → R-S-S-R + 2 Fe$^{+2}$ + 2H$^+$ | (4) |
| 4 R-SH + O$_2$ → 2R-S-S-R + 2H$_2$O | (5) |
| 4 R-SH + SO$_2$ → 2 R-S-S-R + 2 H$_2$O + S | (6a) |
| 2 R-SH + S → R-S-S-R + H$_2$S | (6b) |
| 6 R-SH + SO$_2$ → 3 R-S-S-R + 2 H$_2$O + H$_2$S | (6a + 6b) |

In order to minimize production of polysulfides, when molten sulfur is used as the oxidant, excess mercaptan is used, generally in at least 50–100% excess. The mercaptan then needs to be recovered from the by-product hydrogen sulfide for recycle. Also, the organic disulfide must be recovered from the polysulfides formed.

The use of hydrogen peroxide suffers from the production of 2 moles of water per mole of organic disulfide produced as well as the additional water present with the aqueous solution of hydrogen peroxide. Thus, the reactor volume productivity is low for this method.

The use of a stoichiometric amount of metal ion such as ferric ion (Fe$^{+3}$) is a possibility (reaction 4). However, this process also suffers from low volume productivity of organic disulfide produced per reactor volume. The advantage is that the ferrous ion (Fe$^{+2}$) can be regenerated with air to produce ferric ion (Fe$^{+3}$):

$$2\text{ Fe}^{+2} + \text{O}_2 + 2\text{H}^+ \rightarrow 2\text{Fe}^{+3} + \text{H}_2\text{O}.$$

The use of oxygen as the oxidant (reaction 5) can achieve high conversions (>99.5%) with high organic disulfide selectivity (>98%). The reactions are done in the presence of a basic liquid oxidation catalyst, such as caustic, or triethylamine.

The use of oxygen does have a significant potential safety issue due to the potential for explosions under certain conditions. For instance, at concentrations higher than 10 volume % oxygen, there is a risk of explosion if there is an ignition source present.

The other alternative is to use sulfur dioxide as the oxidant (reaction 6a+6b) in the presence of a liquid catalyst. The reaction is typically carried out in the presence of a basic liquid oxidation catalyst, such as triethylamine (C$_2$H$_5$)$_3$N or boron trifluoride etherate (C$_2$H$_5$)$_2$O●BF$_3$. The use of sulfur dioxide as the oxidant offers the advantage of less explosion hazard as compared to the use of oxygen, and decreased handling difficulties compared to the use of molten sulfur. On the other hand, the use of a liquid basic catalyst in thin method has the disadvantage of lower reactor throughput, lower product yield and lower product selectivity as compared to the use of a solid catalyst in a continuous flow reactor. Also, there is the need to separate the liquid basic catalyst from the liquid product and unreacted liquid feedstock.

Therefore, there is a need to develop a process for oxidizing a mercaptan to an organic disulfide using sulfur dioxide in the presence of a solid catalyst, and, optionally, in the presence of an oxygenated hydrocarbon, and achieving the highest possible yield of organic disulfide.

SUMMARY OF THE INVENTION

It is an object of this invention to provide a process of improved efficiency and economy for producing organic disulfides.

It is another object of this invention to provide a process of improved efficiency and economy for producing organic disulfides by oxidizing mercaptans with sulfur dioxide in the presence of a solid catalyst comprising a solid-porous-basic material.

It is yet another object of this invention to provide a process of improved efficiency and economy for producing organic disulfides by oxidizing mercaptans with sulfur dioxide in the presence of a solid catalyst comprising a solid-porous-acidic material.

It is another object of this invention to provide a process of improved efficiency and economy for producing organic disulfides by oxidizing mercaptans with sulfur dioxide in the presence of an oxygenated hydrocarbon and in the presence of a solid catalyst comprising a solid-porous-basic material.

It is yet another object of this invention to provide a process of improved efficiency and economy for producing organic disulfides by oxidizing mercaptans with sulfur dioxide in the presence of an oxygenated hydrocarbon and in the presence of a solid catalyst comprising a solid-porous-acidic material.

In accordance with an embodiment of the invention, a process useful for producing an organic disulfide is provided. The process can comprise, consist essentially of, or consist of:

a) contacting a hydrocarbon feedstock comprising at least one mercaptan with a catalyst selected from the group consisting of a solid-porous-basic material and a solid-porous-acidic material in the presence of sulfur dioxide and in the substantial absence of a liquid oxidation catalyst to thereby form a hydrocarbon product comprising at least one organic disulfide; and b) recovering said hydrocarbon product.

In accordance with another embodiment of the invention, a process useful for producing an organic disulfide is provided. The process can comprise, consist essentially of, or consist of:

a) contacting a hydrocarbon feedstock comprising at least one mercaptan with a catalyst selected from the group consisting of a solid-porous-basic material and a solid-porous-acidic material in the presence of sulfur dioxide and in the presence of an oxygenated hydrocarbon to thereby form a hydrocarbon product comprising at least one organic disulfide; and b) recovering said hydrocarbon product.

Other objects and advantages will become apparent from the detailed description and the appended claims.

DETAILED DESCRIPTION OF THE INVENTION

The catalyst of the present invention can comprise, consist essentially of, or consist of a material selected from the group consisting of a solid-porous-basic material and a solid-porous-acidic material.

The solid-porous-basic material can be any such material which can catalyze the oxidation of a mercaptan. Suitable solid-porous-basic materials include, but are not limited to, Group IIA metal oxides, according to the CAS version of the Periodic Table of the Elements, (such as, but not limited to, magnesium oxide) and anion or basic ion exchange resins (such as, but not limited to, a polystyrene which contains amino groups).

Suitable anion or basic ion exchange resins include:

Amberlite® IRA-67 ion-exchange resin;

Amberlite® IRA-400 ion-exchange resin;

Amberlite® IRA-400 (Cl) ion-exchange resin;

Amberlite® IRA-410 ion-exchange resin;

Amberlite® IRA-743 ion-exchange resin;

Amberlite® IRA-900 ion-exchange resin: and

Amberlyst® A-21 ion-exchange resin (tertiary amine substituted styrene divinyl benzene copolymer).

The solid-porous-acidic material can be any such material which can catalyze the oxidation of a mercaptan. Suitable solid-porous-acidic materials include, but are not limited to, alumina (preferably γ-alumina); an alumina material consisting essentially of alumina; alumina impregnated with a metal selected from the group consisting of cobalt, molybdenum, tungsten, nickel, the oxides and sulfides of such metals, and combinations of any two or more thereof; and cation or acidic ion-exchange resins such as, but not limited to, carboxylic acid substituted styrene divinyl benzene copolymer or sulfonic acid substituted styrene divinyl benzene copolymer (Amberlyst® 15 ion-exchange resin). The metal impregnated alumina can be prepared by impregnating alumina with the metal (described above) by any means or method known in the art for impregnating metals on alumina, such as, but not limited to, incipient wetness technique. The preferred metal impregnated alumina for use in the invention is cobalt-and-molybdenum impregnated alumina.

Suitable cation or acidic ion exchange resins include:

Amberlite® CG-50 ion-exchange resin;

Amberlite® IR-120(plus) ion-exchange resin;

Amberlite® IR-120(plus) ion-exchange resin, sodium form;

Amberlite® IRC-50 ion-exchange resin;

Amberlite® IRC-50S ion-exchange resin;

Amberlite® IRC-718 ion-exchange resin;

Amberlite® IRP-64 ion-exchange resin; Amberlite® IRP-69 ion-exchange resin; Amberlite® MB-3A ion-exchange resin; Amberlyst® 15 ion-exchange resin;

Amberlyst® 36 ion-exchange resin;

borohydride on Amberlyst® A-26 ion-exchange resin;

bromide on Amberlyst® A-26 ion-exchange resin, chromic acid on Amberlyst® A-26 ion-exchange resin;

flouride on Amberlyst® A-26 ion-exchange resin; and tribromide on Amberlyst® A-26 ion-exchange resin.

When the catalyst is either alumina or metal impregnated alumina, the catalyst can be activated by sulfiding the catalyst under conditions suitable for producing a sulfided catalyst. More particularly, the sulfiding includes passing a flow of gas containing hydrogen sulfide over the catalyst at a temperature in the range of from about 100° C. to about 500° C., preferably in the range of from about 150° C. to about 400° C., and most preferably from 200° C. to 300° C.; and for a time period in the range of from about 0.5 hour to about 30 hours, preferably in the range of from about 0.5 hour to about 20 hours, and most preferably from 1 hour to 15 hours.

The hydrocarbon feedstock of the present invention can comprise, consist essentially of, or consist of one or more mercaptans having the formula of RSH, wherein R is a hydrocarbyl radical having in the range of from about 1 to about 20, preferably from about 1 to about 15, and most preferably from 1 to 12 carbon atoms per radical. Suitable radicals R include alkyl, aryl, alkenyl and cycloalkyl. Each radical R can contain one or more substituents such as, for example, hydroxy, amino, halo, carbonyl, or combinations of any two or more thereof.

Examples of suitable mercaptans include, but are not limited to, methyl mercaptan, ethyl mercaptan, n-propyl mercaptan, isopropyl mercaptan, n-butyl mercaptan, isobutyl mercaptan, sec-butyl mercaptan, tert-butyl mercaptan, n-pentyl mercaptan, isoamyl mercaptan, pentane-3-thiol, n-hexyl mercaptan, isohexyl mercaptan, thiophenol, benzyl mercaptan, n-octyl mercaptan, n-nonyl mercaptan, tert-dodecyl mercaptan, n-dodecyl mercaptan, and combinations of any two or more thereof. The presently preferred mercaptans are the lower alkyl mercaptans such as, for example, methyl mercaptan and n-propyl mercaptan.

The organic disulfide produced in the oxidation of a mercaptan is the corresponding disulfide of the mercaptan. For example, propyl mercaptan is oxidized to dipropyl disulfide. As an additional example, the oxidation of propyl mercaptan and methyl mercaptan in accordance with the present invention produces methylpropyl disulfide along with dimethyl disulfide and dipropyl disulfide. The hydrocarbon feedstock can be contacted with the solid catalyst in the presence of sulfur dioxide and, optionally, in the presence of an oxygenated hydrocarbon.

It is preferable to contact the hydrocarbon feedstock with the solid catalyst in the substantial absence of a liquid oxidation catalyst. Typical liquid oxidation catalysts include, but are not limited to, a caustic (such as sodium hydroxide), boron trifluoride etherate, alkyl amines of the general formula $RNH_2$, dialkyl amines of the general formula $R_2NH$ and trialkylamines of the general formula $R_3N$; wherein each R can be separately selected from any alkyl radical having from 1 to 6 carbon atoms.

A feed mixture comprising, consisting of, or consisting essentially of the hydrocarbon feedstock, Sulfur dioxide and, optionally, the oxygenated hydrocarbon, is contacted with the catalyst contained in an oxidation zone.

Generally, sulfur dioxide, and, optionally, the oxygenated hydrocarbon, is mixed with the hydrocarbon feedstock to form the feed mixture which is contacted with the catalyst contained in the oxidation zone. The concentration of the sulfur dioxide in the feed mixture during this contacting step shall be such as to provide a mercaptan to sulfur dioxide molar ratio of at least about 1:1, preferably at least about 6:1, more preferably in the range of from about 8:1 to about 100:1, and most preferably in the range of from 10:1 to 60:1. At mercaptan to sulfur dioxide molar ratios below about 6:1 a buildup of elemental sulfur in the reaction vessel can occur which can lead to plugging problems or to catalyst deactivation.

It is believed that the presence of an oxygenated hydrocarbon serves to remove water from the solid catalyst, during continuous flow mode, which results in decreased activity loss and, consequently, longer catalyst life.

The oxygenated hydrocarbon of the present invention can comprise, consist of, or consist essentially of a compound selected from the group consisting of an ether, an alcohol, and combinations thereof.

Examples of suitable ethers include ether hydrocarbons having from 2 to 10, preferably from 2 to 6, and most preferably from 2 to 4 carbon atoms per molecule, and combinations of any two or more thereof.

Examples of suitable alcohols include alcoholic hydrocarbons having from 1 to 10, preferably from 1 to 6, and most preferably from 1 to 4 carbon atoms per molecule, and combinations of any two or more thereof. The most preferred oxygenated hydrocarbon is methanol.

The concentration of the oxygenated hydrocarbon in the feed mixture during the contacting step can be such as to provide an oxygenated hydrocarbon weight % in the range of from about 2 weight % to about 25 weight %, preferably from about 2 weight % to about 20 weight %, and most preferably from 5 weight % to 15 weight %, based on the total weight of the feed mixture.

The hydrocarbon feedstock, sulfur dioxide, and optionally, the oxygenated hydrocarbon, can be contacted with the inventive catalyst by any suitable manner. The contacting step can be operated as a batch process step or, preferably, as a continuous process step. In the latter operation, a solid catalyst bed or a moving catalyst bed or a fluidized catalyst bed can be employed. Any of these operational modes has advantages and disadvantages, and those skilled in the art can select the one most suitable for a particular feed and catalyst.

The contacting step is preferably carried out within an oxidation zone, wherein is contained the catalyst, and under reaction conditions that suitably promote oxidation of at least a portion of the mercaptans of the hydrocarbon feedstock. The contacting pressure of the oxidation zone is in the range of from about atmospheric to about 1500 psig, preferably in the range of from about 200 psig to about 700 psig, and most preferably in the range of from 400 psig to 600 psig.

The flow rate at which the hydrocarbon feedstock is charged to the oxidation zone is such as to provide a weight hourly space velocity ("WHSV") in the range of from about 0.01 hour$^{-1}$ to about 1000 hour$^{-1}$. The term "weight hourly space velocity", as used herein, shall mean the numerical ratio of the rate at which a hydrocarbon feedstock is charged to the oxidation zone in pounds per hour divided by the pounds of catalyst contained in the oxidation zone to which the hydrocarbon feedstock is charged. The preferred WHSV of the hydrocarbon feedstock to the oxidation zone is in the range of from about 0.05 hour$^{-1}$ to about 10 hour$^{-1}$ and, most preferably, in the range of from 0.05 hour$^{-1}$ to 5 hour$^{-1}$.

The reaction temperature of the oxidation zone depends on the catalyst employed in the oxidation zone, but generally ranges from about 20° C. to about 300° C.

When the catalyst is a Group IIA metal oxide the reaction temperature is more particularly in the range of from about 150° C. to about 300° C., preferably in the range of from about 150° C. to about 200° C., and most preferably in the range of from 160° C. to 180° C.

When the catalyst is alumina the reaction temperature is more particularly in the range of from about 80° C. to about 170° C., preferably in the range of from about 100° C. to about 170° C., and most preferably in the range of from 120° C. to 160° C.

When the catalyst is metal impregnated alumina the reaction temperature is more particularly in the range of from about 100° C. to about 170° C., preferably in the range of from about 130° C. to about 165° C., and most preferably in the range of from 150° C. to 160° C.

When the catalyst is a cation or acidic ion-exchange resin the reaction temperature is more particularly in the range of from about 20° C. to about 100° C., preferably in the range of from about 70° C. to about 95° C., and most preferably in the range of from 80° C. to 90° C.

When the catalyst is an anion or basic ion-exchange resin the reaction temperature is more particularly in the range of from about 20° C. to about 100° C., preferably in the range of from about 70° C. to about 95° C., and most preferably in the range of from 80° C. to 90° C.

The following example is presented to further illustrate the invention and is not to be construed as unduly limiting its scope.

EXAMPLE

This example illustrates the oxidation of mercaptans with sulfur dioxide when contacted with the catalysts described above, and, for Run 12, in the presence of added methanol.

In Run 1,100 cm$^3$ (71.02 grams) of ground magnesium oxide extrudate, obtained from Catalyst Resources, Inc. under product designation Lynx® 5205 catalyst, were placed into a stainless steel tube reactor (length: about 34 inches; inner diameter: about 0.75 inch). A 311 mL (3.4 moles) quantity of n-propyl mercaptan and 147 grams (2.3 moles) of sulfur dioxide (SO$_2$) were combined in a stainless steel feed tank forming a feed mixture to yield a mole ratio of n-propyl mercaptan to SO$_2$ of 1.5. The feed tank was shaken several times immediately prior to initiating the run. The reactor was heated to about 175° C., as measured at the center of the catalyst bed, and the feed mixture was pumped into the reactor at a WHSV for n-propyl mercaptan of 1. The reactor pressure wag maintained at 500 psig. The reactor effluent was collected in a Jurgenson sight glass and samples from the sight glass were sent to a gas chromatograph (GC) approximately every 20–25 minutes for analysis. Following sampling, the sight glass contents were dumped to the flare to avoid contamination of the next sample. Test data results obtained after about 50 minutes on stream are summarized in the Table.

In Run 2, a 300 ml autoclave reactor was purged with nitrogen followed by the addition of 5 grams of magnesium oxide (powdered) obtained from Fisher Scientific. A 160 mL (1.7 moles) quantity of n-propyl mercaptan and 22 grams (0.3 moles) of liquid sulfur dioxide were added to the autoclave reactor. The autoclave reactor was heated, with stirring, to 85° C. and maintained there for 30 minutes at which time sample A was taken and analyzed by a GC. The autoclave reactor was then heated, with stirring, to a temperature in the range of from about 150° C. to about 155° C. and maintained there for 35 minutes at which time the contents of the autoclave reactor were cooled to 60° C. and sample B was taken and analyzed by a GC. The autoclave reactor was then heated, with stirring, to a temperature in the range of from about 197° C. to about 203° C. and maintained there for 31 minutes at which time the contents of the autoclave reactor were cooled to 60° C. and sample C was taken and analyzed by a GC. The autoclave reactor was then heated, with stirring, to a temperature in the range of from about 217° C. to about 225° C. and maintained there for 26 minutes at which time the contents of the autoclave reactor were cooled to 60° C. and sample D was taken and analyzed by a GC. Test data results obtained for samples A through D are summarized in the Table.

In Run 3, a 300 ml autoclave reactor was purged with nitrogen followed by the addition of 5 grams of Amberlyst® A-21 ion-exchange resin manufactured by Rohm and Haas Company and obtained from Aldrich Chemical Company. A 161 mL (1.8 moles) quantity of n-propyl mercaptan and 25 grams (0.4 mole) of liquid sulfur dioxide were added to the autoclave reactor. The autoclave reactor was heated, with stirring, to about 85° C. and maintained there for about 2 hours and a sample was taken and analyzed using a GC. Test data results obtained are summarized in the Table.

In Run 4, 50.14 grams of Amberlyst® 15 ion-exchange resin (sulfonated divinylbenzene crosslinked polystyrene), manufactured by Rohm and Haas Company and obtained from Aldrich Chemical Company, were placed into a stainless steel tube reactor (length: about 34 inches; inner diameter: about 0.75 inch). A 760 gram (15.8 moles) quantity of methyl mercaptan and 127 grams (2.0 moles) of $SO_2$ were combined in a stainless steel feed tank forming a feed mixture to yield a mole ratio of methyl mercaptan to $SO_2$ of 7.9. The feed tank was shaken several times immediately prior to initiating the run. The reactor was heated to about 50° C., as measured at the center of the catalyst bed, and the feed mixture was pumped into the reactor at a WHSV for methyl mercaptan of 1. The reactor pressure was maintained at 200 psig. The reactor effluent was collected in a Jurgenson sight glass and samples from the sight glass were sent to a GC approximately every 20–25 minutes for analysis. Following sampling, the sight glass contents were dumped to the flare to avoid contamination of the next sample. Test data results obtained after about 50 minutes on stream are summarized in the Table.

In Run 5, 100 cm$^3$ (63.84 grams) of 1/20" gamma alumina extrudates, obtained from Engelhard Corporation under product designation AL-3945E, were placed into a stainless steel tube reactor (length: about 34 inches; inner diameter: about 0.75 inch). The gamma alumina was treated with a flow of hydrogen sulfide (WHSV=4) for 3 hours at 260° C. A 600 gram (12.4 moles) quantity of methyl mercaptan and 83 grams (1.3 moles) of $SO_2$ were combined in a stainless steel feed tank forming a feed mixture to yield a mole ratio of methyl mercaptan to $SO_2$ of 9.5. The feed tank was shaken several times immediately prior to initiating the run. The reactor was heated to about 100° C., as measured at the center of the catalyst bed, and the feed mixture was pumped into the reactor at a WHSV for methyl mercaptan of 1. The reactor pressure was maintained at 500 psig. The reactor effluent was collected in a Jurgenson sight glass and samples from the sight glass were sent to a GC approximately every 20–25 minutes for analysis. Following sampling, the sight glass contents were dumped to the flare to avoid contamination of the next sample. Test data results obtained after about 50 minutes on stream are summarized in the Table.

In Run 6, 80.2 cm$^3$ (51.19 grams) of 1/20" gamma alumina extrudates, obtained from Engelhard Corporation under product designation AL-3945E, were placed into a stainless steel tube reactor (length: about 34 inches; inner diameter: about 0.75 inch). The gamma alumina was treated with a flow of hydrogen sulfide (WHSV=4) for 3 hours at 260° C. An 800 gram (16.7 moles) quantity of methyl mercaptan and 107 grams (1.7 moles) of $SO_2$ were combined in a stainless steel feed tank forming a feed mixture to yield a mole ratio of methyl mercaptan to $SO_2$ of 9.8. The feed tank was shaken several times immediately prior to initiating the run. The reactor was heated to about 150° C., as measured at the center of the catalyst bed, and the feed mixture was pumped into the reactor at a WHSV for methyl mercaptan of 1. The reactor pressure was maintained at 500 psig. The reactor effluent was collected in a Jurgenson sight glass and samples from the sight glass were sent to a GC approximately every 20–25 minutes for analysis. Following sampling, the sight glass contents were dumped to the flare to avoid contamination of the next sample. Test data results obtained after about 50 minutes on stream are summarized in the Table.

In Run 7, 100 cm$^3$ (64.39 grams) of Co/Mo on gamma alumina (1.33 mm extrudate), obtained from Criterion Catalyst Company under product designation Criterion 447TL, were placed into a stainless steel tube reactor (length: about 34 inches; inner diameter: about 0.75 inch). The Co/Mo on gamma alumina was treated with a flow of hydrogen sulfide (WHSV=4) for 3 hours at 260° C. A 415 mL (4.6 moles) quantity of n-propyl mercaptan and 147 grams (2.3 moles) of $SO_2$ were combined in a stainless steel feed tank forming a feed mixture to yield a mole ratio of n-propyl mercaptan to $SO_2$ of 2. The feed tank was shaken several times immediately prior to initiating the run. The reactor was heated to about 167° C., as measured at the center of the catalyst bed, and the feed mixture was pumped into the reactor at a WHSV for n-propyl mercaptan of 1. The reactor pressure was maintained at 500 psig. The reactor effluent was collected in a Jurgenson sight glass and samples from the sight glass were sent to a GC approximately every 20–25 minutes for analysis. Following sampling, the sight glass contents were dumped to the flare to avoid contamination of the next sample. Test data results obtained after about 50 minutes on stream are summarized in the Table.

In Run 8, 100 cm$^3$ (64.55 grams) of Co/Mo on gamma alumina (1.33 mm extrudate), obtained from Criterion Catalyst Company under product designation Criterion 447 TL, were placed into a stainless steel tube reactor (length: about 34 inches; inner diameter: about 0.75 inch). The Co/Mo on gamma alumina was treated with a flow of hydrogen sulfide (WHSV=4) for 3 hours at 260° C. A 200 gram (4.17 moles) quantity of methyl mercaptan and 49.6 grams (0.78 moles) of $SO_2$ were combined in a stainless steel feed tank forming a feed mixture to yield a mole ratio of methyl mercaptan to $SO_2$ of 5.3. The feed tank was shaken several times immediately prior to initiating the run. The reactor was heated to about 103° C., as measured at the center of the catalyst bed, and the feed mixture was pumped into the reactor at a WHSV for methyl mercaptan of 1. The reactor pressure was maintained at 500 psig. The reactor effluent was collected in a Jurgenson sight glass and samples from the sight glass were sent to a GC approximately every 20–25 minutes for analysis. Following sampling, the sight glass contents were dumped to the flare to avoid contamination of the next sample. Test data result obtained after about 50 minutes on stream are summarized in the Table.

In Run 9, a 300 ml autoclave reactor was purged with nitrogen followed by the addition of 150 mL (1.64 moles) n-propyl mercaptan and 28.6 grams (0.4 mole) of liquid $SO_2$ to the autoclave reactor (without any catalyst). The autoclave reactor was heated, with stirring, to about 200° C. and maintained there for 33 minutes. Stirring was then stopped and the contents of the autoclave reactor were cooled to 35° C. and a sample was taken and analyzed using a GC. Test data results obtained are summarized in the Table.

In Run 10, 100 cm$^3$ of inert 3mm solid glass beads, obtained from Corning Inc., were placed into a stainless steel tube reactor (length: about 34 inches; inner diameter: about 0.75 inch). An 800 gram (16.7 moles) quantity of methyl mercaptan and 183 grams (2.86 moles) of $SO_2$ were combined in a stainless steel feed tank forming a feed mixture to yield a mole ratio of methyl mercaptan to $SO_2$ of 5.8. The feed tank was shaken several times immediately prior to initiating the run. The reactor was heated to about 210° C., as measured at the center of the catalyst bed, and the feed mixture was pumped into the reactor at a WHSV for methyl mercaptan of 1. The reactor pressure was maintained at 500 psig. The reactor effluent was collected in a Jurgenson sight glass and samples from the sight glass were sent to a GC approximately every 20–25 minutes for analysis. Following sampling, the sight glass contents were dumped to the flare to avoid contamination of the next sample. Test data results obtained after about 50 minutes on steam are summarized in the Table.

In Run 11, 100 cm³ (33.58 grams) of silica gel chunks, obtained from Linde AG Zentralverwaltung, Wiesbaden, Germany under product designation G-57 silica, were placed into a stainless steel tube reactor (length: about 34 inches; inner diameter: about 0.75 inch). A 220 gram (4.58 moles) quantity of methyl mercaptan and 34.2 grams (0.53 moles) of $SO_2$ were combined in a stainless steel feed tank forming a feed mixture to yield a mole ratio of methyl mercaptan to $SO_2$ of 8.6. The feed tank was shaken several times immediately prior to initiating the run. The reactor was heated to about 105° C., as measured at the center of the catalyst bed, and the feed mixture was pumped into the reactor at a WHSV for methyl mercaptan of 1. The reactor pressure was maintained at 500 psig. The reactor effluent was collected in a Jurgenson sight glass and samples from the sight glass were sent to a GC approximately every 20–25 minutes for analysis. Following sampling, the sight glass contents were dumped to the flare to avoid contamination of the next sample. Test data results obtained after about 50 minutes on stream are summarized in the Table.

In Run 12, 80.2 cm³ (51.19 grams) of 1/20" gamma alumina extrudates, obtained from Engelhard Corporation under product designation AL-3945E, were placed into a stainless steel tube reactor (length: about 34 inches; inner diameter: about 0.75 inch). The gamma alumina was treated with a flow of hydrogen sulfide (WHSV=4) for 3 hours at 260° C. A 760 gram (15.8 moles) quantity of methyl mercaptan, 101 grams (1.6 moles) of $SO_2$ and 86 grams (2.7 moles) of methanol were combined in a stainless steel feed tank forming a feed mixture to yield a mole ratio of methyl mercaptan to $SO_2$ of 9.8 and a methanol weight % of 9.1 wt. %. The feed tank was shaken several times immediately prior to initiating the run. The reactor was heated to about 150° C., as measured at the center of the catalyst bed, and the feed mixture was pumped into the reactor at a WHSV for methyl mercaptan of 1. The reactor pressure was maintained at 500 psig. The reactor effluent was collected in a Jurgenson sight glass and samples from the sight glass were sent to a GC approximately every 20–25 minutes for analysis. Following sampling, the sight glass contents were dumped to the flare to avoid contamination of the next sample. Test data results obtained after about 50 minutes on stream are summarized in the Table.

TABLE

| Run | Catalyst | Reactor Type | Mercaptan Converted | Measured Mercaptan Conversion Mole % | Highest Possible Mercaptan Conversion[1] Mole % | Relative Mercaptan Conversion[2] % | Dialkyl disulfide Selectivity[3] Mole % | Dialkyl disulfide/ Dialkyl trisulfide Mole Ratio in Product |
|---|---|---|---|---|---|---|---|---|
| 1 | MgO | CF | n-PM | 26% | 100% | 26% | >99% | >99:1 |
| 2 | MgO | A | n-PM | | | | | |
| Sample A | | | | 10% | 100% | 10% | 92% | >99:1 |
| B | | | | 11.2% | 100% | 11.2% | 88% | 95:5 |
| C | | | | 38.1% | 100% | 38.1% | 69% | 75:25 |
| D | | | | 65.7% | 100% | 65.7% | 87% | 91:9 |
| 3 | Amberlyst ® A-21 ion-exchange resin | A | n-PM | 13% | 100% | 13% | 85% | 93:7 |
| 4 | Amberlyst ® 15 ion-exchange resin | CF | MM | 24% | 75% | 32% | 68% | 68:32 |
| 5 | γ-alumina (@ 100° C.) | CF | MM | 47.3% | 63% | 75% | 97% | 97:3 |
| 6 | γ-alumina (@ 150° C.) | CF | MM | 52.5% | 61% | 86% | 98% | 98:2 |
| 7 | Co/Mo on alumina | CF | n-PM | 98% | 100% | 98% | 39% | 39:61 |
| 8 | Co/Mo on alumina | CF | MM | 91% | 100% | 91% | 95% | 95:5 |
| 9 | None | A | n-PM | 6.7% | 100% | 6.7% | 67% | 87:13 |
| 10 | Inert glass beads | CF | MM | 2% | 100% | 2% | 70% | 70:30 |
| 11 | G-57 silica | CF | MM | 0% | 69% | 0% | — | — |
| 12 | γ-alumina (@ 150° C.) | CF | MM (with 9.1 wt. % methanol in feed) | 60.4 | 61% | 99% | 98% | 98:2 |

CF = continuous flow; A = autoclave; n-PM = n-propyl mercaptan; MM = methyl mercaptan
[1]Relative Mercaptan Conversion = Measured Mercaptan Conversion/Highest Possible Mercaptan Conversion, multiplied by 100.
[2]Highest Possible Mercaptan Conversion = The highest mercaptan conversion possible given the amount of $SO_2$ present. For instance, 1 mole of $SO_2$ is required to theoretically completely react 6 moles of mercaptan. With a mercaptan/$SO_2$ mole ratio greater than 6:1, the highest possib
+e, mercaptan conversion will be less than 100% and; with a mercaptan/$SO_2$ mole ratio less than 6:1, the highest possible mercaptan conversion is 100%.
[3]Dialkyl disulfide selectivity = the mole % of Dialkyl disulfide in the product divided by the mole % Measured Mercaptan Conversion, multiplied by 100.

The test data presented in the Table show that use of the inventive catalysts-Group IIA metal (such as magnesium oxide), anion or basic ion-exchange resin (such as Amberlyst® A-21 ion-exchange resin), cation or acidic ion-exchange resin (such as Amberlyst® 15 ion-exchange resin), alumina (such as γ-alumina) and metal impregnated alumina (such as Co/Mo on alumina)—in Runs 1–8 and 12 resulted in significant relative mercaptan conversions (from 10% to 99%) and, in all but Run 7, high dialkyl disulfide selectivities (from 67% to >99%) and high dialkyl disulfide to dialkyl trisulfide mole ratios (from 68:32 to >99:1).

Also, the inventive catalysts used in Runs 1–8 demonstrated increases in mercaptan conversion of from 49% to 1363% over Run 9 wherein no catalyst was used.

It was thought that perhaps any solid support might serve as a catalyst in the inventive process. Run 10 was then performed using inert (neutral) glass beads, which have virtually no pore volume and low surface area, in the inventive process. As shown in the Table, the inert glass beads were basically ineffective as a catalyst in converting methyl mercaptan to dimethyl disulfide.

It was then thought that perhaps the pore volume and surface area of the inventive catalysts was alone responsible for their effectiveness in converting mercaptans into dialkyl disulfides. Run 11 was then performed using inert (neutral) G-57 silica, which has a pore volume of 1.2 cm³/gram and a surface area of 302 m²/gram, in the inventive process. As shown in the Table, the inert-porous G-57 silica was ineffective as a catalyst in converting methyl mercaptan to dimethyl disulfide.

In addition, the relative mercaptan conversion in inventive Run 12, which included the addition of methanol to the methyl mercaptan and $SO_2$ feed, was 99% which is significantly higher than the 86% relative mercaptan conversion of inventive Run 6 which used the same catalyst and operating conditions as inventive Run 12 but without added methanol.

From the test data in the Table, it is readily apparent that the inventive catalysts are effective in producing organic disulfides when used in the oxidation of mercaptans with sulfur dioxide and that the presence of an oxygenated hydrocarbon, such as methanol, increases the oxidation of mercaptans with sulfur dioxide.

Reasonable variations, modifications, and adaptations can be made within the scope of the disclosure and the appended claims without departing from the scope of this invention.

That which is claimed is:

1. A process for oxidizing a mercaptan comprising:
   a) contacting under oxidizing conditions a reaction mixture consisting essentially of a hydrocarbon feedstock, at least one mercaptan, sulfur dioxide and a catalyst selected from 1) a solid catalyst consisting essentially of alumina and a solid catalyst selected from the group consisting of 2) a Group IIA metal oxide; 3) an impregnated alumina impregnated with a metal selected from the group consisting of cobalt, molybdenum, tungsten, nickel and combinations of any two or more thereof; 4) an acidic ion-exchange resin; 5) a basic ion-exchange resin; and 6) combinations of any two or more of 1–5 to thereby form a hydrocarbon product comprising at least one organic disulfide; and
   b) recovering said hydrocarbon product.

2. A process in accordance with claim 1 wherein the mole ratio of said at least one mercaptan to said sulfur dioxide is at least about 1:1.

3. A process in accordance with claim 1 wherein the mole ratio of said at least one mercaptan to said sulfur dioxide is at least about 6:1.

4. A process in accordance with claim 1 wherein said at least one mercaptan comprises a compound selected from the group consisting of methyl mercaptan, ethyl mercaptan, n-propyl mercaptan, isopropyl mercaptan, n-butyl mercaptan, isobutyl mercaptan, sec-butyl mercaptan, tert-butyl mercaptan, n-pentyl mercaptan, isoamyl mercaptan, pentane-3-thiol, n-hexyl mercaptan, isohexyl mercaptan, thiophenol, benzyl mercaptan, n-octyl mercaptan, n-nonyl mercaptan, n-dodecyl mercaptan, tert-dodecyl mercaptan, and combinations of any two or more thereof.

5. A process in accordance with claim 1 wherein said catalyst comprises said Group IIA metal oxide.

6. A process in accordance with claim 5 wherein said catalyst comprises magnesium oxide.

7. A process in accordance with claim 1 wherein said catalyst comprises said solid catalyst consisting essentially of alumina.

8. A process in accordance with claim 7 wherein said alumina material is γ-alumina.

9. A process in accordance with claim 7 wherein the solid catalyst consisting essentially of alumina is sulfided prior to contacting step a).

10. A process in accordance with claim 1 wherein said catalyst comprises said impregnated alumina.

11. A process in accordance with claim 10 wherein said catalyst is sulfided prior to contacting step (a).

12. A process in accordance with claim 1 wherein said catalyst comprises a cobalt-and-molybdenum impregnated alumina.

13. A process in accordance with claim 12 wherein said catalyst is sulfided prior to contacting step (a).

14. A process in accordance with claim 1 wherein said catalyst comprises said acidic ion-exchange resin.

15. A process in accordance with claim 14 wherein said acidic ion-exchange resin is selected from the group consisting of carboxylic acid substituted styrene divinyl benzene copolymer, sulfonic acid substituted styrene divinyl benzene copolymer and combinations thereof.

16. A process in accordance with claim 14 wherein said acidic ion-exchange resin is sulfonic acid substituted styrene divinyl benzene copolymer.

17. A process in accordance with claim 1 wherein said catalyst comprises a basic ion-exchange resin.

18. A process in accordance with claim 17 wherein said basic ion-exchange resin is a tertiary amine substituted styrene divinyl benzene copolymer.

19. A process in accordance with claim 1 wherein said contacting of said hydrocarbon feedstock of step a) and said recovering said hydrocarbon product of step b) are performed in a continuous flow mode.

20. A process in accordance with claim 1 wherein said contacting of said hydrocarbon feedstock of step a) and said recovering said hydrocarbon product of step b) are performed in a batch mode.

21. A process in accordance with claim 1 wherein said contacting said hydrocarbon feedstock of step a) is performed at a temperature in the range of from about 20° C. to about 300° C., a pressure in the range of from about atmospheric to about 1500 psig and a WHSV in the range of from about 0.01 hr.$^{-1}$ to about 1000 hr.$^{-1}$.

22. A process in accordance with claim 5 wherein said contacting said hydrocarbon feedstock of step a) is performed at a temperature in the range of from about 150° C. to about 300° C., a pressure in the range of from about atmospheric to about 1500 psig and a WHSV in the range of from about 0.01 hr.$^{-1}$ to about 1000 hr.$^{-1}$.

23. A process in accordance with claim 5 wherein said contacting said hydrocarbon feedstock of step a) is performed at a temperature in the range of from about 150° C. to about 200° C., a pressure in the range of from about 200 psig to about 700 psig and a WHSV in the range of from about 0.05 hr.$^{-1}$ to about 10 hr.$^{-1}$.

24. A process in accordance with claim 5 wherein said contacting said hydrocarbon feedstock of step a) is performed at a temperature in the range of from 160° C. to 180° C., a pressure in the range of from 400 psig to 600 psig and a WHSV in the range of from 0.05 hr.$^{-1}$ to 5 hr.$^{-1}$.

25. A process in accordance with claim 7 wherein said contacting said hydrocarbon feedstock of step a) is performed at a temperature in the range of from about 80° C. to about 170° C., a pressure in the range of from about atmospheric to about 1500 psig and a WHSV in the range of from about 0.01 hr.$^{-1}$ to about 1000 hr.$^{-1}$.

26. A process in accordance with claim 7 wherein said contacting said hydrocarbon feedstock of step a) is performed at a temperature in the range of from about 100° C. to about 170° C., a pressure in the range of from about 200 psig to about 700 psig and a WHSV in the range of from about 0.05 hr.$^{-1}$ to about 10 hr.$^{-1}$.

27. A process in accordance with claim 7 wherein said contacting said hydrocarbon feedstock of step a) is performed at a temperature in the range of from 120° C. to 160° C., a pressure in the range of from 400 psig to 600 psig and a WHSV in the range of from 0.05 hr.$^{-1}$ to 5 hr.$^{-1}$.

28. A process in accordance with claim 10 wherein said contacting said hydrocarbon feedstock of step a) is performed at a temperature in the range of from about 100° C. to about 170° C., a pressure in the range of from about atmospheric to about 1500 psig and a WHSV in the range of from about 0.01 hr.$^{-1}$ to about 1000 hr.$^{-1}$.

29. A process in accordance with claim 10 wherein said contacting said hydrocarbon feedstock of step a) is performed at a temperature in the range of from about 130° C. to about 165° C., a pressure in the range of from about 200 psig to about 700 psig and a WHSV in the range of from about 0.5 hr.$^{-1}$ to about 10 hr.$^{-1}$.

30. A process in accordance with claim 10 wherein said contacting said hydrocarbon feedstock of step a) is performed at a temperature in the range of from 150° C. to 160° C., a pressure in the range of from 400 psig to 600 psig and a WHSV in the range of from 0.05 hr.$^{-1}$ to 5 hr.$^{-1}$.

31. A process in accordance with claim 14 wherein said contacting said hydrocarbon feedstock of step a) is performed at a temperature in the range of from about 20° C. to about 100° C., a pressure in the range of from about atmospheric to about 1500 psig and a WHSV in the range of from about 0.01 hr.$^{-1}$ to about 1000 hr.$^{-1}$.

32. A process in accordance with claim 14 wherein said contacting said hydrocarbon feedstock of step a) is performed at a temperature in the range of from about 70° C. to about 95° C., a pressure in the range of from about 200 psig to about 700 psig and a WHSV in the range of from about 0.05 hr.$^{-1}$ to about 10 hr.$^{-1}$.

33. A process in accordance with claim 14 wherein said contacting said hydrocarbon feedstock of step a) is performed at a temperature in the range of from 80° C. to 90° C., a pressure in the range of from 400 psig to 600 psig and a WHSV in the range of from 0.05 hr.$^{-1}$ to 5 hr.$^{-1}$.

34. A process in accordance with claim 17 wherein said contacting said hydrocarbon feedstock of step a) is performed at a temperature in the range of from about 20° C. to about 100° C., a pressure in the range of from about atmospheric to about 15800 psig and a WHSV in the range of from about 0.01 hr.$^{-1}$ to about 1000hr.$^{-1}$.

35. A process in accordance with claim 17 wherein said contacting said hydrocarbon feedstock of step a) is performed at a temperature in the range of from about 70° C. to about 95° C., a pressure in the range of from about 200 psig to about 700 psig and a WHSV in the range of from about 0.05 hr.$^{-1}$ to about 10 hr.$^{-1}$.

36. A process in accordance with claim 17 wherein said contacting said hydrocarbon feedstock of step a) is performed at a temperature in the range of from 80° C. to 90° C., a pressure in the range of from 400 psig to 600 psig and a WHSV in the range of from 0.05 hr.$^{-1}$ to 5 hr.$^{-1}$.

37. A process for oxidizing a mercaptan comprising:
   a) contacting under oxidizing conditions a reaction mixture consisting essentially of a hydrocarbon feedstock, at least one mercaptan, sulfur dioxide, oxygenated hydrocarbon and a solid catalyst contained in an oxidation zone wherein said catalyst is selected from 1) a solid catalyst consisting essentially of alumina and a solid catalyst selected from the group consisting of 2) a Group IIA metal oxide; 3) an impregnated alumina impregnated with a metal selected from the group consisting of cobalt, molybdenum, tungsten, nickel and combinations of any two or more thereof, 4) an acidic ion-exchange resin; 5) a basic ion-exchange resin; and 6) combinations of any two or more of 1–5; to thereby form a hydrocarbon product comprising at least one organic disulfide; and
   b) recovering said hydrocarbon product.

38. A process in accordance with claim 37 wherein step a) is performed in the substantial absence of a liquid oxidation catalyst.

39. A process in accordance with claim 37 wherein said oxygenated hydrocarbon comprises a compound selected from the group consisting of an ether, an alcohol, and combinations thereof.

40. A process in accordance with claim 39 wherein said ether is selected from the group consisting of ether hydrocarbons having from 2 to 10 carbon atoms per molecule, and combinations of any two or more thereof.

41. A process in accordance with claim 39 wherein said alcohol is selected from the group consisting of alcoholic hydrocarbons having from 1 to 10 carbons atoms per molecule, and combinations of any two or more thereof.

42. A process in accordance with claim 37 wherein said oxygenated hydrocarbon is methanol.

43. A process in accordance with claim 37 wherein the weight % of said oxygenated hydrocarbon contained in said oxidation zone is in the range of from about 2 weight % to about 25 weight %, based on the combined weight of said hydrocarbon feedstock, said sulfur dioxide, and said oxygenated hydrocarbon contained within said oxidation zone.

44. A process in accordance with claim 37 wherein the weight % of said oxygenated hydrocarbon contained in said oxidation zone is in the range of from about 2 weight % to about 20 weight %, based on the combined weight of said hydrocarbon feedstock, said sulfur dioxide, and said oxygenated hydrocarbon contained within said oxidation zone.

45. A process in accordance with claim 37 wherein the weight % of said oxygenated hydrocarbon contained in said oxidation zone is in the range of from about 5 weight % to 15 weight %, based on the combined weight of said hydrocarbon feedstock, said sulfur dioxide, and said oxygenated hydrocarbon contained within said oxidation zone.

46. A process in accordance with claim 37 wherein the mole ratio of said at least one mercaptan to said sulfur dioxide is at least about 1:1.

47. A process in accordance with claim 37 wherein the mole ratio of said at least one mercaptan to said sulfur dioxide is at least about 6:1.

48. A process in accordance with claim 37 wherein said at least one mercaptan comprises a compound selected from the group consisting of methyl mercaptan, ethyl mercaptan, n-propyl mercaptan, isopropyl mercaptan, n-butyl mercaptan, isobutyl mercaptan, sec-butyl mercaptan, tert-butyl mercaptan, n-pentyl mercaptan, isoamyl mercaptan, pentane-3-thiol, n-hexyl mercaptan, isohexyl mercaptan, thiophenol, benzyl mercaptan, n-octyl mercaptan, n-nonyl mercaptan, n-dodecyl mercaptan, tert-dodecyl mercaptan, and combinations of any two or more thereof.

49. A process in accordance with claim 37 wherein said catalyst comprises a Group IIA metal oxide.

50. A process in accordance with claim 37 wherein said catalyst comprises magnesium oxide.

51. A process in accordance with claim 37 wherein said catalyst comprises alumina.

52. A process in accordance with claim 51 wherein said alumina is γ-alumina.

53. A process in accordance with claim 51 wherein said alumina is sulfided prior to contacting step (a).

54. A process in accordance with claim 37 wherein said catalyst comprises alumina impregnated with a metal selected from the group consisting of cobalt, molybdenum, tungsten, nickel and combinations of any two or more thereof.

55. A process in accordance with claim 54 wherein said catalyst is sulfided prior to contacting step (a).

56. A process in accordance with claim 37 wherein said catalyst comprises a cobalt-and-molybdenum impregnated alumina.

57. A process in accordance with claim 56 wherein said catalyst is sulfided prior to contacting Step (a).

58. A process in accordance with claim 37 wherein said catalyst comprises an acidic ion-exchange resin.

59. A process in accordance with claim 58 wherein said acidic ion-exchange resin is selected from the group consisting of carboxylic acid substituted styrene divinyl benzene copolymer, sulfonic acid substituted styrene divinyl benzene copolymer and combinations thereof.

60. A process in accordance with claim 59 wherein said acidic ion-exchange resin is sulfonic acid substituted styrene divinyl benzene copolymer.

61. A process in accordance with claim 37 wherein said catalyst comprises a basic ion-exchange resin.

62. A process in accordance with claim 61 wherein said basic ion-exchange resin is a tertiary amine substituted styrene divinyl benzene copolymer.

63. A process in accordance with claim 37 wherein said contacting of said hydrocarbon feedstock of step a) and said recovering said hydrocarbon product of step b) are performed in a continuous flow mode.

64. A process in accordance with claim 37 wherein said contacting of said hydrocarbon feedstock of step a) and said recovering said hydrocarbon product of step b) are performed in a batch mode.

65. A process in accordance with claim 37 wherein said contacting said hydrocarbon feedstock of step a) is performed at a temperature in the range of from about 20° C. to about 300° C., a pressure in the range of from about atmospheric to about 1500 psig and a WHSV in the range of from about 0.01 hr.$^{-1}$ to about 1000 hr.$^{-1}$.

66. A process in accordance with claim 49 wherein said contacting said hydrocarbon feedstock of step a) is performed at a temperature in the range of from about 150° C. to about 300° C., a pressure in the range of from about atmospheric to about 1500 psig and a WHSV in the range of from about 0.01hr.$^{-1}$ to about 1000 hr.$^{-1}$.

67. A process in accordance with claim 49 wherein said contacting said hydrocarbon feedstock of step a) is performed at a temperature in the range of from about 150° C. to about 200° C., a pressure in the range of from about 200 psig to about 700 psig and a WHSV in the range of from about 0.05 hr.$^{-1}$ to about 10 hr.$^{-1}$.

68. A process in accordance with claim 49 wherein said contacting said hydrocarbon feedstock of step a) is performed at a temperature in the range of from 160° C. to 180° C., a pressure in the range of from 400 psig to 600 psig and a WHSV in the range of from 0.05 hr.$^{-1}$ to 5 hr.$^{-1}$.

69. A process in accordance with claim 51 wherein said contacting said hydrocarbon feedstock of step a) is performed at a temperature in the range of from about 80° C. to about 170° C., a pressure in the range of from about atmospheric to about 1500 psig and a WHSV in the range of from about 0.01 hr.$^{-1}$ to about 1000 hr.$^{-1}$.

70. A process in accordance with claim 51 wherein said contacting said hydrocarbon feedstock of step a) is performed at a temperature in the range of from about 100° C. to about 170° C., a pressure in the range of from about 200 psig to about 700 psig and a WHSV in the range of from about 0.05 hr.$^{-1}$ to about 10 hr.$^{-1}$.

71. A process in accordance with claim 51 wherein said contacting said hydrocarbon feedstock of step a) is performed at a temperature in the range of from 120° C. to 160° C., a pressure in the range of from 400 psig to 600 psig and a WHSV in the range of from 0.05 hr.$^{-1}$ to 5 hr.$^{-1}$.

72. A process in accordance with claim 54 wherein said contacting said hydrocarbon feedstock of step a) is performed at a temperature in the range of from about 100° C. to about 170° C., a pressure in the range of from about atmospheric to about 1500 psig and a WHSV in the range of from about 0.01 hr.$^{-1}$ to about 1000 hr.$^{-1}$.

73. A process in accordance with claim 54 wherein said contacting said hydrocarbon feedstock of step a) is performed at a temperature in the range of from about 130° C. to about 165° C., a pressure in the range of from about 200 psig to about 700 psig and a WHSV in the range of from about 0.05 hr.$^{-1}$ to about 10 hr.$^{-1}$.

74. A process in accordance with claim 54 wherein said contacting said hydrocarbon feedstock of step a) is performed at a temperature in the range of from 150° C. to 160° C., a pressure in the range of from 400 psig to 600 psig and a WHSV in the range of from 0.05 hr.$^{-1}$ to 5 hr.$^{-1}$.

75. A process in accordance with claim 58 wherein said contacting said hydrocarbon feedstock of step a) is performed at a temperature in the range of from about 20° C. to about 100° C., a pressure in the range of from about atmospheric to about 1500 psig and a WHSV in the range of from about 0.01 hr.$^{-1}$ to about 1000 hr.$^{-1}$.

76. A process in accordance with claim 58 wherein said contacting said hydrocarbon feedstock of step a) is performed at a temperature in the range of from about 70° C. to about 95° C., a pressure in the range of from about 200 psig to about 700 psig and a WHSV in the range of from about 0.05 hr.$^{-1}$ to about 10 hr.$^{-1}$.

77. A process in accordance with claim 58 wherein said contacting said hydrocarbon feedstock of step a) is performed at a temperature in the range of from 80° C. to 90° C., a pressure in the range of from 400 psig to 600 psig and a WHSV in the range of from 0.05 hr.$^{-1}$ to 5 hr.$^{-1}$.

78. A process in accordance with claim 61 wherein said contacting said hydrocarbon feedstock of step a) is performed at a temperature in the range of from about 20° C. to about 100° C., a pressure in the range of from about atmospheric to about 15800 psig and a WHSV in the range of from about 0.01 hr.$^{-1}$ to about 1000 hr.$^{-1}$.

79. A process in accordance with claim 61 wherein said contacting said hydrocarbon feedstock of step a) is performed at a temperature in the range of from about 70° C. to about 95° C., a pressure in the range of from about 200 psig to about 700 psig and a WHSV in the range of from about 0.05 hr.$^{-1}$ to about 10 hr.$^{-1}$.

80. A process in accordance with claim 61 wherein said contacting said hydrocarbon feedstock of step a) is performed at a temperature in the range of from 80° C. to 90° C., a pressure in the range of from 400 psig to 600 psig and a WHSV in the range of from 0.05 hr.$^{-1}$ to 5 hr.$^{-1}$.

\* \* \* \* \*